US010620202B2

(12) United States Patent
Samadpour

(10) Patent No.: US 10,620,202 B2
(45) Date of Patent: Apr. 14, 2020

(54) METHOD FOR CONFIRMING THE PRESENCE OF AN ANALYTE

(75) Inventor: Mansour Samadpour, Seattle, WA (US)

(73) Assignee: Institute for Environmental Health, Inc., Lake Forest Park, WA (US)

(*) Notice: Subject to any disclaimer, the term of this patent is extended or adjusted under 35 U.S.C. 154(b) by 897 days.

(21) Appl. No.: 12/430,804

(22) Filed: Apr. 27, 2009

(65) Prior Publication Data

US 2009/0291446 A1    Nov. 26, 2009

Related U.S. Application Data

(63) Continuation-in-part of application No. 11/107,458, filed on Apr. 15, 2005, now Pat. No. 8,956,826.

(60) Provisional application No. 60/562,302, filed on Apr. 15, 2004, provisional application No. 61/047,999, filed on Apr. 25, 2008.

(51) Int. Cl.
| C12Q 1/68 | (2018.01) |
| G01N 33/569 | (2006.01) |
| G01N 33/543 | (2006.01) |
| C12Q 1/689 | (2018.01) |

(52) U.S. Cl.
CPC ....... *G01N 33/56916* (2013.01); *C12Q 1/689* (2013.01); *G01N 33/54326* (2013.01); *C12Q 2600/16* (2013.01); *G01N 2333/245* (2013.01); *Y02A 50/52* (2018.01)

(58) Field of Classification Search
CPC .................. G01N 33/54326; G01N 33/56916
USPC ......................................................... 435/34
See application file for complete search history.

(56) References Cited

U.S. PATENT DOCUMENTS

| 5,402,363 A | 3/1995 | Siebert |
| 6,268,143 B1* | 7/2001 | Oberst .................. C12Q 1/689 435/134 |
| 7,052,831 B2 | 5/2006 | Fletcher et al. |
| 7,118,870 B2 | 10/2006 | Field |
| 7,226,739 B2 | 6/2007 | Ecker et al. |
| 7,255,992 B2 | 8/2007 | Ecker et al. |
| 7,534,584 B2 | 5/2009 | Samadpour |
| 7,919,232 B2 | 4/2011 | Samadpour |
| 8,389,233 B2 | 3/2013 | Samadpour |
| 8,822,143 B2 | 9/2014 | Samadpour |
| 8,956,826 B2 | 2/2015 | Samadpour |
| 2002/0090626 A1 | 7/2002 | Hyldig-Nielsen |
| 2002/0115074 A1 | 8/2002 | Dattagupta |
| 2002/0151700 A1 | 10/2002 | Farwick |
| 2005/0170346 A1 | 8/2005 | Westh et al. |
| 2006/0051751 A1* | 3/2006 | Wang et al. ............ 435/6 |
| 2006/0115824 A1 | 6/2006 | Samadpour |
| 2006/0205040 A1 | 9/2006 | Sampath |
| 2007/0287156 A1 | 12/2007 | Pourmand et al. |
| 2008/0003564 A1 | 1/2008 | Chen et al. |
| 2008/0026953 A1 | 1/2008 | Gala et al. |
| 2008/0038769 A1 | 2/2008 | Bernardi et al. |
| 2008/0096189 A1 | 4/2008 | Boone et al. |
| 2008/0096236 A1 | 4/2008 | Koulchin et al. |

OTHER PUBLICATIONS

Ochoa et al., 2005, Anal. Chem., 77:5258-5267.*
Salehi TZ, Tadjbakhsh H, Atashparvar N, Nadalian MG, Mahzounieh MR. Detection and identification of *Salmonella typhimurium* in bovine diarrhoeic fecal samples by immunomagnetic separation and multiplex PCR assay. Zoonoses Public Health. 2007; 54(6-7): 231-6. (Year: 2007).*
Gooding, C.M. and Choudary, P.V., 1998. Detection of *Escherichia coli* O157: H7 in ground beef in eight hours. Journal of microbiological methods, 34(2), pp. 89-98. (Year: 1998).*
Wang L, Li Y, Mustaphai A. Rapid and simultaneous quantitation of *Escherichia coli* 0157:H7, *Salmonella*, and Shigella in ground beef by multiplex real-time PCR and immunomagnetic separation. J Food Prot. Jun. 2007; 70(6):1366-72. (Year: 2007).*
International Search Report for International (PCT) Application No. PCT/US09/41839, dated Aug. 24, 2009.
Written Opinion for International (PCT) Application No. PCT/US09/41839, dated Aug. 24, 2009.
International Preliminary Report on Patentability for International (PCT) Application No. PCT/US2009/41839, dated Nov. 4, 2010.
Acheson, D.W.K., "How Does *Escherichia coli* O157:H7 Testing in Meat Compare With What we are Seeing Clinically?" Journal of Food Protection 63(6):819-821, 2000.
Baldwin, B., et al., "Detection and Enumeration of Aromatic Oxygenase Genes by Multiplex and Real-Time PCR," Applied and Environmental Microbiology 69(6):3350-3358, Jun. 2003.
Barney, M., et al., "Riboprinting and 16S rRNA Gene Sequencing for Identification of Brewery Pediococcus Isolates," Applied and Environmental Microbiology 67(2):553-560, Feb. 2001.
Behari, J., et al., "pepA, a Gene Mediating pH Regulation of Virulence Genes in Vibrio cholerae," Journal of Bacteriology 183(1):178-188, Jan. 2001.
Bekal, S., et al., "Rapid Identification of *Escherichia coli* Pathotypes by Virulence Gene Detection with DNA Microarrays," Journal of Clinical Microbiology 41(5):2113-2125, May 2003.
Boer, E.d., and R.R. Beumer, "Methodology for Detection and Typing of Foodborne Microorganisms," International Journal of Food Microbiology 50:119-130, 1999.
Call, D., et al., "Detecting and Genotyping *Escherichia coli* O157:H7 Using Multiplexed PCR and Nucleic Acid Microarrays," International Journal of Food Microbiology 67:71-80, 2001.
Carvalho, A.C.T., et al., "Molecular Characterization of Invasive and Noninvasive Campylobacter jejuni and *Campylocacter coli* Isolates," Journal of Clinical Microbiology 39(4):1353-1359, Apr. 2001.
Conner, C.P., et al., "Differential Patterns of Acquired Virulence Genes Distinguish *Salmonella* Strains," The Proceedings of the National Academy of Sciences USA 95:4641-4645, Apr. 1998.

(Continued)

*Primary Examiner* — Gary Benzion
*Assistant Examiner* — Olayinka A Oyeyemi
(74) *Attorney, Agent, or Firm* — Barry L. Davison; Davis Wright Tremaine LLP

(57) ABSTRACT

The invention provides methods and kits for the rapid confirmation of an initial analyte test result. In a preferred embodiment, the process confirms the presence of a given microbial target in a mixed culture, or a mixed enrichment media, even when the competing organisms in the mix belong to related species, or are various biotypes of the same species.

9 Claims, No Drawings

(56) References Cited

OTHER PUBLICATIONS

Darwin, K.H., and V.L. Miller, "Molecular Basis of the Interaction of *Salmonella* With the Intestinal Mucosa," Clinical Microbiology Reviews 12(3):405-428, Jul. 1999.
Doyle, M.P., and J.L. Schoeni, "Isolation of *Escherichia coli* 0157:H7 From Retail Fresh Meats," Applied and Environmental Microbiology 53(10):2394-2396, Oct. 1987.
Faruque, S.M., et al., "Epidemiology, Genetics, and Ecology of Toxigenic Vibrio cholerae," Microbiology and Molecular Biology Reviews 62(4):1301-1314, Dec. 1998.
Hale, T.L., "Genetic Basis of Virulence in *Shigella* Species," Microbiological Reviews 55(2):206-224, Jun. 1991.
Heller, K.J., "Probiotic Bacteria in Fermented Foods: Product Characteristics and Starter Organisms," American Journal of Clinical Nutrition 73(Suppl):374S-379S, 2001.
Hendrickson, E.R., et al., "Molecular Analysis of Dehalococcoides 16S Ribosomal DNA From Chloroethene-Contaminated Sites Throughout North America and Europe," Applied and Environmental Microbiology 68(2):485-495, Feb. 2002.
Horz, H.-P., et al., "Detection of Methanotroph Diversity on Roots of Submerged Rice Plants by Molecular Retrieval of pmoA, mmoX, mxaF, and 16S rRNA and Ribosomal DNA, Including pmoA-Based Terminal Restriction Fragment Length Polymorphism Profiling," Applied and Environmental Microbiology 67(9):4177-4185, Sep. 2001.
Ibekwe, A.M., et al., "Multiplex Fluorogenic Real-Time PCR for Detection and Quantification of *Escherichia coli* O157:H7 in Dairy Wastewater Wetlands," Applied and Environmental Microbiology 68(10):4853-4862, Oct. 2002.
Ke, D., et al., "Development of a PCR Assay for Rapid Detection of Enterococci," Journal of Clinical Microbiology 37 (11):3497-3503, Nov. 1999.
Mcmahon, K.D., et al, "Polyphosphate Kinase From Activated Sludge Performing Enhanced Biological Phosphorus Removal," Applied and Environmental Microbiology 68(10):4971-4978, Oct. 2002.
Mesarch, M.B., et al., "Development of Catechol 2,3-Dioxygenase-Specific Primers for Monitoring Bioremediation by Competitive Quantitative PCR," Applied and Environmental Microbiology 66(2):678-683, Feb. 2000.
Millemann, Y., et al., "Evaluation of IS200-PCR and Comparison With Other Molecular Markers to Trace *Salmonella enterica* subsp. *enterica* Serotype Typhimurium Bovine Isolates From Farm to Meat," Journal of Clinical Microbiology 38(6):2204-2209, Jun. 2000.
Nataro, J.P., and J.B. Kaper, "Diarrheagenic *Escherichia coli*," Clinical Microbiology Reviews 11(1):142-201, Jan. 1998.
Osek, J., "Development of a Multiplex PCR Approach for the Identification of Shiga Toxin-Producing *Escherichia coli* Strains and Their Major Virulence Factor Genes," Journal of Applied Microbiology 95:1217-1225, 2003.
Padhye, N.V., and M.P. Doyle, "*Escherichia coli* O157:H7: Epidemiology, Pathogenesis, and Methods for Detection in Food," Journal of Food Protection 55(7):555-565, Jul. 1992.
Porwollik, S., et al., "Characterization of *Salmonella enterica* Subspecies I *genovars* by Use of Microarrays," Journal of Bacteriology 186(17):5883-5898, Sep. 2004.

Riley, D.E., et al., "Detection of Variable DNA Repeats in Diverse Eukaryotic Microorganisms by a Single Set of Polymerase Chain Reaction Primers," Journal of Clinical Microbiology 29(12):2746-2751, Dec. 1991.
Rivera, I.N.G., et al., "Genotypes Associated with Virulence in Environmental Isolates of Vibrio cholerae," Applied and Environmental Microbiology 67(6):2421-2429, Jun. 2001.
Samadpour, M., et al., "Evaluation of DNA Probes for Detection of Shiga-Like-Toxin-Producing *Escherichia coli* in Food and Calf Fecal Samples," Applied and Environmental Microbiology 56(5):1212-1215, May 1990.
Samadpour, M., et al., "Occurrence of Shiga-Like Toxin-Producing *Escherichia coli* in Retail Fresh Seafood, Beef, Lamb, Pork, and Poultry from Grocery Stores in Seattle, Washington," Applied and Environmental Microbiology 60(3):1038-1040, Mar. 1994.
Sharma, N.K., et al., "Development of a Single-Reaction Multiplex PCR Toxin Typing Assay for *Staphylococcus aureus* Strains," Applied and Environmental Microbiology 66(4):1347-1353, Apr. 2000.
Somer, L., and Y. Kashi, "A PCR Method Based on 16S rRNA Sequence for Simultaneous Detection of the Genus *Listeria* and the Species *Listeria monocytogenes* in Food Products," Journal of Food Protection 66(9):1658-1665, 2003.
Suzuki, K., et al., "Genetic Characterization and Specific Detection of Beer-Spoilage *Lactobacillus* sp. LA2 and Related Strains," Journal of Applied Microbiology 96:677-683, 2004.
Suzuki, K., et al., "Genetic Characterization of Non-Spoilage Variant Isolated From Beer-Spoilage Lactobacillus Brevis ABBC45," Journal of Applied Microbiology 96:946-953, 2004.
Suzuki, K., et al., "Genetic Marker for Differentiating Beer-Spoilage Ability of Lactobacillus paracollinoides Strains," Journal of Applied Microbiology 97:712-718, 2004.
Takahashi, T., et al., "Classification and Identification of Strains of Lactobacillus brevis Based on Electrophoretic Characterization of D-Lactate Dehydrogenase: Relationship Between D-Lactate Dehydrogenase and Beer-Spoilage Ability," Journal of Bioscience and Bioengineering 88(5):500-506, 1999.
Vankerckhoven, V., et al., "Development of a Multiplex PCR for the Detection of asa1, gelE, cylA, esp, and hyl Genes in Enterococci and Survey for Virulence Determinants Among European Hospital Isolates of Enterococcus faecium," Journal of Clinical Microbiology 42(10):4473-4479, Oct. 2004.
Wikipedia, Definition of "Quotient," <http://en.wikipedia.org/wiki/Quotient> [retrieved Dec. 29, 2008], 3 pages.
Yamasaki, M., et al., "Genetic and Immunochemical Characterization of Thiocyanate-Degrading Bacteria in Lake Water," Applied and Environmental Microbiology 68(2):942-946, Feb. 2002.
International Search Report and Written Opinion dated Nov. 10, 2005, in International Patent Application No. PCT/US2005/013047, filed Apr. 15, 2005, 10 pages.
European Search Report dated Jan. 30, 2009, in European Patent Application No. 05 737 668.3, filed Apr. 15, 2005, 8 pages.
European Search Report dated Sep. 9, 2011, in European Patent Application No. 11152709.9, filed Apr. 15, 2005, 11 pages.
"HACCP Principles & Application Guidelines," National Advisory Committee on Microbiological Criteria for Foods, Adopted Aug. 14, 1997, <https://www.fda.gov/Food/GuidanceRegulation/HACCP/ucm2006801.htm> [retrieved Apr. 15, 2019], 24 pages.

\* cited by examiner

METHOD FOR CONFIRMING THE PRESENCE OF AN ANALYTE

CROSS REFERENCE TO RELATED APPLICATION

This application claims the benefit of priority under 35 U.S.C. § 119(e) to U.S. Provisional Patent Application No. 61/047,999 filed Apr. 25, 2008, and is a continuation in part of U.S. patent application Ser. No. 11/107,458, filed Apr. 15, 2005, which claims the benefit of priority under 35 U.S.C. § 119(e) to U.S. Provisional Patent Application No. 60/562,302, filed Apr. 15, 2004. These priority applications are incorporated herein, in their entirety, by reference.

TECHNICAL FIELD

The invention relates to the field of microbiology and more specifically relates to methods, articles, and kits for confirming the presence of an analyte. More particularly, the invention relates to a method and system that employs means to corroborate the findings of an initial positive assay result by a second robust alternative assay protocol.

BACKGROUND OF INVENTION

Various approaches have been described for performing assays to determine the presence or concentration of a specific microbial analyte, such as pathogenic microbial contamination of food. Frequently, a two-step process is followed wherein a first, rapid screening method is used to obtain initial assay results with negative results accepted as is. When a positive result is obtained, it is characterized as a "presumptive positive" result until it can be confirmed by the application of a second, alternative assay protocol applied to the sample. This process is followed because it is highly desirable, and in some cases required by government regulation, to corroborate a positive result in order to prevent the unnecessary recall and needless disposal of material implicated as containing a pathogen, such as food products.

In order for an alternative analysis protocol to be effective for the purpose of confirmation, it must meet several performance criteria. It should be selective, i.e. it should correctly identify a sample as not containing a target pathogenic microbe when in fact the microbe is not present. It should be sensitive, i.e. it should correctly identify a sample as containing a target pathogenic microbe when in fact the contaminant is present. It should have a low detection limit, i.e. it should give a positive result even when only a small number of target pathogen microbes are present.

Traditionally, these performance criteria have been met by applying cultural analysis protocols involving culture enrichment, selective and differential plating, and additional biochemical and serological methods. However, such cultural protocols suffer from the drawback that the time required to complete the analysis can easily extend over several days. This makes it difficult to acquire information in a timely manner upon which to base a decision regarding the recall or disposal of a perishable material implicated as potentially containing a pathogenic microbial contaminant by presumptive positive results obtained using a rapid screening method.

Thus, what is needed in the art is an alternative analysis method which meets the performance criteria necessary to corroborate presumptive positive results, and which can be completed rapidly enough to generate a result which can be acted upon in a timely manner.

Similarly, the present art of rapid screening suffers from the fact that either single signals are to be used to detect a given pathogen, in which case not all of the targets will be detected (they may not all have the target signal), or if multiple signals (multiplexes) are used to detect the pathogen/organism of interest, in matrixes such as food, water, environmental samples, and some clinical samples (such as urine and feces) where a diverse group of organisms are present, there is a distinct possibility that that the multiplex screen will detect a composite signal from more than one organism. For instance, if a food sample contains a non-toxigenic, eae negative *E. coli* O157, an enteropathogenic *E. coli*, and an *E. coli*, producing Shiga toxin, and the sample is screened with a multiplex PCR that targets eae, rfb, and stx, to detect pathogenic *E. coli* O157, then a composite signal consisting of three bands (eae, rfb, and stx) will be observed. In this instance, the data indicates that a pathogenic *E. coli* O157 is detected in the sample, but in reality, the toxin and the eae signal come from two other organisms. The presently available techniques will consider the sample a presumptive positive and it is then subjected to culture confirmation which will take 3-5 days.

SUMMARY OF INVENTION

The present invention (referred to sometimes herein as Molecular Confirmation) allows for rapid confirmation of the initial analyte test results. Typically the process takes from about one to about three hours. Furthermore, in a preferred embodiment, the process will allow for confirmation of the presence of a given microbial target in a mixed culture, or a mixed enrichment media, even when the competing organisms in the mix belong to related species, or are various biotypes of the same species. For example, the methods of the present invention allow differentiation between *E. coli* O157 and non-O157 Shiga toxin-producing *E. coli* in the same sample. Additionally, these methods can differentiate between *Listeria monocytogenes* and other *Listeria* species in the same sample. Also, these methods can identify multi-drug resistant *salmonella* from other *Salmonella* or other multi-drug resistant bacteria in the same sample.

The invention solves the problems of the prior art by providing protocols to meet the performance criteria and generate a result rapidly so that subsequent decisions can be made in a timely manner. Various embodiments of the present invention are generally complementary to two broad classes of rapid screening methods which enrich a sample prior to application of an assay protocol. Herein 'enrich' is understood to consist of the steps of adding growth media to a sample and incubating the sample at an appropriate temperature and for an appropriate period of time, so that the target organism is given an opportunity to reproduce and reach a concentration level commensurate with the detecting ability of the assay protocol.

The first broad class of rapid screening methods which rely on enriching a sample use the polymerase chain reaction (PCR). Generally, the enriched sample is lysed to release the DNA contained in organisms present. DNA primer templates are added which are composed of specific nucleotide sequences that complement known portions of genes which are unique to the target analyte organism. A DNA polymerase and nucleotides are added, and in vitro enzymatic replication of DNA occurs. As replicate DNA strands are generated, they serve as templates for the next cycle of replication. Generally, cycles are defined by alternating heating and cooling of the sample to allow the DNA to physically separate and join, with the thermal cycling conditions providing another means of enhancing selectivity. With PCR it is possible to amplify a single or a few copies of a specific strand of DNA across several orders of magnitude, generating millions or more copies of the specific strand of DNA. Thereafter, the DNA is generally separated using agarose gel chromatography, and the DNA product, if present, is visualized by the application of a dye to the agarose gel.

The second broad class of rapid screening methods which rely on enriching a sample are immunoassays, which rely on reactions between antibodies and their corresponding antigens which are unique to the target analyte organism. For example, one group of methods are enzyme-linked immunosorbent assays (ELISAs) in which an antigen associated with the target analyte organism is affixed to a surface, and then an antibody specific to that antigen is washed over the surface so that it can bind to the antigen. The antibody is linked to an enzyme which is capable of converting a substance that is added to some detectable signal. A second group of methods are immunochromatographic assays (also called lateral flow devices, or LFDs) in which a test sample flows through a matrix via capillary action. The sample encounters a visualizing reagent (e.g. calorimetric or fluorometric) which then migrates with the sample. The sample encounters lines or zones which have been pretreated with either an antibody or antigen that binds to the target analyte, if present, and associated visualizing reagent.

Various embodiments of the present invention rely on applying one or more of seven principles to define a rapid confirmatory analysis protocol. These principles are:

(1) The presumptive positive sample will be subjected to PCR reaction(s) which are designed to amplify multiple targets
(2) The targets include at least two genes which are restricted mostly to or are unique in the target organism.
(3) When, in any one of the target genes, there are variations in the sequences among the target organisms and closely related biotypes, at least one PCR reaction should target the conserved regions of the molecule, and another PCR reaction should target the specific variation(s) which are unique to the target organism.
(4) In it's preferred embodiment, each PCR/multiplex confirmation reaction should be conducted with and without immunomagnetic separation, using specific antibodies to the target organism.
(5) Additional target genes for the target organism may be included to increase the confidence in the confirmation, or better define the target organism.
(6) In it's preferred embodiment for each target gene, two PCR reactions will be designed, each corresponding to different primer sequences. This will allow for redundancy and also protect against point mutation in primer sequences, and failure of one reaction.
(7) Other confirmatory rapid tests for specific targets, such as immunochemical test (lateral flow devices), toxin assays, and specific biochemicals may also be used to complement the molecular confirmation reactions.

In a specific aspect of the invention, a method of confirming the presence of contamination in a sample is provided that includes contacting a first portion of the sample with a magnetic bead coated with an antibody that specifically recognizes a microorganism and providing a second portion of the sample that has not been contacted with the magnetic bead coated with an antibody that has contacted the first portion of the sample and assaying the first portion of the sample for the presence of a contaminant microorganism by 4-band multiplex PCR assay using PCR primers complementary to four nucleic acid targets indicative of microbial contaminant, while separately assaying the first portion of the sample for the presence of a contaminant microorganism by 5-band multiplex PCR assay using PCR primers complementary to four nucleic acid targets indicative of microbial contaminant and one nucleic acid target specific to a suspected microbe, while separately assaying the second portion of the sample for the presence of a contaminant microorganism by 4-band multiplex PCR assay using PCR primers complementary to four nucleic acid targets indicative of microbial contaminant, while separately assaying the second portion of the sample for the presence of a contaminant microorganism by 5-band multiplex PCR assay using PCR primers complementary to four nucleic acid targets indicative of microbial contaminant and one nucleic acid target specific to a suspected microbe and comparing the results of the PCR assays wherein: a) the detection of three nucleic acid targets in the four band multiplex PCR assay conducted on the first portion of the sample is indicative of microbial contamination of the sample, or b) the detection of one nucleic acid target in the four band multiplex PCR assay conducted on the first portion of the sample and the detection of three nucleic acid targets in the four band multiplex PCR assay conducted on the second portion of the sample is indicative of is indicative of the absence of the suspected microbe. In this aspect of the invention, the sample may be contacted with a growth media to enrich the sample in a contaminant present in the sample. This aspect of the invention may be conducted on a sample that has been analyzed for the presence of a contaminant microorganism by 4-band multiplex PCR assay using PCR primers complementary to four gene targets associated with the microbial contaminant, prior to contacting a first portion of the sample with a magnetic bead.

Another aspect of the invention provides a kit for performing an analytical test for detecting the presence of and distinguishing between *E. Coli* O157 and non-O157 shinga toxin producing *E. Coli* in a biological sample suspected of containing one or both. The kit includes an analytical test device having a plurality of wells, wherein the wells do not communicate with each other (wherein each well includes a filter stack, the filter stack including (i) a porous membrane having an upper surface and a lower surface; and (ii) an absorbent material, wherein the lower surface of the porous membrane and the absorbent material are in physical contact and in fluid communication, and wherein upon contact of a biological fluid sample suspected of containing one or both of *E. Coli* O157 and non-O157 shinga toxin producing *E. Coli* with said porous membrane, said fluid is able to flow through said membrane into said absorbent material, such that at least a portion of said *E. Coli* O157 and non-O157 shinga toxin producing *E. Coli* present in said biological fluid sample bind to said porous membrane); a first detection reagent capable of recognizing *E. Coli* O157; a second detection reagent capable of recognizing non-O157 shinga toxin producing *E. Coli*; and a reagent capable of generating a signal upon detection of one or both of *E. Coli* O157 and non-O157 shinga toxin producing *E. Coli*.

Another aspect of the invention provides a method for obtaining confirmation of the presence of a microbial analyte in less than three hours, by adding growth media to a sample of bacteria cells believed to contain a target analyte organism and incubating the sample at an appropriate temperature for an appropriate period of time, so that the target organism is given an opportunity to reproduce and to reach a concentration level sufficient to detect a sought after analyte; lysing bacterial cells to release the DNA contained therein, adding DNA primer templates composed of specific nucleotide sequences that complement known portions of genes which are unique to the target analyte organism; adding DNA polymerase and nucleotides to achieve in vitro enzymatic replication of desired DNA pieces; amplifying said DNA pieces by several orders of magnitude to generate at least a million copies of the DNA piece; separating said DNA pieces by using agarose gel chromatography, and adding a dye to the DNA product to determine visually the presence of said DNA.

Another aspect of the invention provides a method of detecting at least one substance of interest in a biological sample by providing a biological liquid sample suspected of comprising the substance(s) of interest; contacting the biological sample in a sufficient amount to with at least one specific binding pair member that is capable of binding, either directly or indirectly, the substance(s) of interest; and maintaining such contact for between about one and about 3 hours; and detecting the presence or absence of a complex comprising the specific binding pair member(s) and the substance(s) of interest, wherein the presence of at least one complex indicates the presence of at least one of the substances of interest in the biological sample.

The following references are incorporated herein in their entireties to enable one of skill in the art to appreciate various aspects of the present invention: Patent publication No. 20080096236 to Koulchin; 20080096189 to Boone; 20080038769 to Bernardi; 20080026953 to Gala, as well as U.S. Pat. No. 7,255,992 to Ecker, et al.; U.S. Pat. No. 7,226,739 to Ecker, et al.; U.S. Pat. No. 7,052,831 to Fletcher, et al.

DESCRIPTION OF EMBODIMENTS

The present invention is drawn to methods of screening and monitoring for microbial growth and contaminants including the use of secondary analysis methods needed for rapid screening and verification of primary or preliminary testing results. In conducting testing for microbial growth or contamination, an initial or preliminary testing result may be obtained by sampling and/or testing a subject or good by any one of several testing methodologies as described in U.S. Patent Publication No. 200/0115824, such as "presence/absence" tests or a plurality of the same.

Processes and systems to which the testing and verification methods of the instant application may be applicable include, but are not limited to: food production; manufacturing; processing; storage; transportation and distribution; with respect to microbial pathogens—process sanitation, environmental contaminants, and spoilage organisms; with respect to fermentation processes—determining purity of the seed stock and fermentation contaminants; aseptic processing (e.g., food and pharmaceutical; with respect to sterility and environmental control); water treatment (e.g., with respect to microbiological quality of the raw and treated water, and control of the organisms throughout the distribution system); wastewater treatment (e.g., with respect to microbiological quality of the treated wastewater and biosolids, control of the treatment process, control of the aerobic and anaerobic digesters, and assessment of the impact of the discharged wastewater and application of bio-solids on the receiving environments); control of microbial contaminants and assessment of their impact in the indoor environment and indoor air quality assessment studies; environmental microbiology (e.g., with respect to monitoring the microbiological quality of shellfish, shellfish beds and cultured aquatic organisms, assessing the microbiological quality of recreational waters and swimming beaches, assessing the microbiological quality of bodies of water, conducting impact assessment of point and non-point-sources); feed microbiology (e.g., in determining the microbiological quality and safety of the feed); soil microbiology (e.g., in assessing the overall microbiology and population structure of soil organisms, in assessing target organisms that can indicate environmental contamination or organic and inorganic reservoirs (e.g., oil fields)).

If a presumptive positive result is obtained using the rapid screening method, molecular confirmation is conducted using test methods that may include, but are not limited to, multiplex PCR reaction(s), DNA chips, dot blots, multi- and single-target lateral flow devices, and combinations thereof. In preferred aspects, assays suitable for detection of pathogenic or microbial contamination may include the use of immunoassays, nucleic acid amplification-based assays, PCR-based assays, nucleic acid hybridization-based assays, bio-sensor assays, immunostaining-microscopy-based assays, nucleic acid-array-based assays, DNA chip-based assays, bacteriophage-detection-based assays, classical microbiology-based assays, and chemical or biochemical assays based on the detection of compounds associated with particular target organisms or groups of target organisms, and combinations thereof.

In a specific application for the target analyte organism *E. coli* O157, a 4-band multiplex PCR assay is used as an initial, rapid screening method. The four PCR assay targets are gene segments known to be associated with *E. coli* O157. These assay targets are rfb, eae, stx1 and stx2. After enrichment of a sample to allow the growth of the target organisms to the detection level, the enrichment is screened with the 4-band multiplex PCR assay.

If a presumptive positive result is obtained using the rapid screening method, molecular confirmation is conducted using two other multiplex PCR reactions (one with four targets and one with five targets). Each PCR assay contains targets for stx1, stx2, rfb, eae (one universal one gamma). One of the multiplex PCR assays also contains an additional gene unique to O157. Molecular Confirmation is done using the two multiplexes, with and without immunomagnetic separation using magnetic beads coated with anti-O157 antibodies.

The key to separation of O157 from non-O157 STEC and determination of whether there is a true O157 versus a composite signal, is determined by a comparison of the PCR assays with and without the beads and the fact that O157 carries gamma eae. If a four band multiplex assay with the magnetic beads shows rfb, eae, and stx, this indicates that a true pathogenic O157 *E. coli* in the enrichment, however if it only shows rfb, while the non-magnetic separated enrichment shows the rfb, eae, and stx, then we know that there is a non-toxigenic, eae-negative O157 in the enrichment.

The same principle is used for *Listeria monocytogenes* vs. *Listeria* species in the same enrichment and for toxigenic *Bacillus cereus* versus other Bacilli in the same enrichment, and for *Salmonella*/multi-drug resistant *Salmonella* versus a multi-drug resistant bacteria in the same enrichment. The same assay principles are used for other pathogenic, spoilage, indicators, biodegradative organisms, and pharmaceutical platform/producer strains of organisms.

A fifth specific application again targets *Salmonella* spp. Immunomagnetic Separation (IMS) is used to purify and concentrate the sample prior to conducting a confirmation 3-band multiplex PCR assay; however, the immunomagnetic beads in this case are coated with antibodies which bind specifically to *Salmonella* spp.

In a sixth specific application, the pathogenic microbes *Listeria* spp. and *Listeria monocytogenes* (LM) are targeted using a 4-band multiplex PCR assay as a rapid screening method. Two of the PCR assay targets are gene segments known to be associated with LM, while the remaining two are known to be associated with *Listeria* spp. If a presumptive positive result is obtained using the rapid screening method for LM, a second 2-band multiplex PCR assay is used to corroborate the presumptive positive result and provide confirmation. If a presumptive positive result is obtained for *Listeria* spp. another independent 2-band multiplex PCR assay is used to corroborate the presumptive positive result and provide confirmation A seventh specific application again targets *Listeria* spp. and *Listeria monocytogenes*. IMS is used to purify and concentrate the sample prior to applying one or both of the confirmation 2-band multiplex PCR assays; however, the immunomagnetic beads in this case are coated with antibodies which bind specifically to *Listeria* spp., of which LM is one type.

Another aspect of the present invention is directed to a rapid confirmation method for microorganisms, in mixed cultures or enrichment cultures. The method allows for rapid confirmation of the presence of single or multiple target organisms in the same mixture. The method has built in redundancy that increases the confidence in the results. It can also confirms and characterizes the organisms in a single step.

These microorganisms may include a microbe or pathogen such as *Escherichia coli* O157:H7 (*E. coli* O157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella, Listeria, Yersinia, Campylobacter*, Clostridial species, *Staphylococcus* spp.; frank and opportunistic bacterial, fungal, viral, parsitic pathogens; indicator organisms including heterotrophes, generic *E. coli*, total and fecal coliforms and *enterococcus*; spoilage organisms including *Pseudomonas*; indicator molecules including glial fibillary acid protein (GFAP), transmissable spongiform encephalopathy (TSE) agents (prions), including bovine spongiform encephalopathy (BSE) agents, scrapie, chronic wasting disease; and combinations thereof. Additional microbe sor pathogensare selected from the group consisting of *Staph. aureus, Bacillus cereus*, and *Clostridium botulinum, Clostridium perfringes, Vibrio cholerae* and *V. parahemolyticus, Yersinia enterocolitica, Yersinia pestis, Brucella. Francisella, Aeromonas* and *Plesiomonas, Citrobacter, Enterobacter, Klebsiella, Morganella, Proteus, Providencia, Serratia*, and *Shigella*.

Organisms that are particularly suited for testing in one or more aspects of the present invention include the following:
*Bacillus anthracis*
*Campylobacter coli*
*Campylobacter jujuni*
*Campylobacter lari*
Coliforms
*E. coli* O157
*E. coli*, Stx-producing (STEC)
*E. coli*, Stx-producing with intimin
*E. coli*, verotoxin producing
*Listeria grayi*
*Listeria innocua*
*Listeria ivanovii*
*Listeria monocytogenes*
*Listeria seeligeri*
*Listeria* spp.
*Listeria welshimeri*
*Salmonella* spp.
Staphylococcal enterotoxins A, B, C (C1, C2, C3), D and E
*Staphylococcus aureus*
Yeast and Mold Each publication or patent cited herein is incorporated herein by reference in its entirety.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of confirming the presence of a particular target contaminant microorganism or of a false positive in a sample, comprising:

contacting a first portion of a sample that may be contaminated by a plurality of genetically distinct microorganisms with a magnetic bead coated with an antibody that specifically recognizes a particular target contaminant microorganism to provide an antibody-captured first sample portion;

providing a second portion of the sample that has not been contacted with the magnetic bead coated with the antibody;

assaying the antibody-captured first sample portion for the presence of the target contaminant microorganism by using a multiplex PCR assay using PCR primers complementary to nucleic acid targets indicative of the presence of the target contaminant microorganism, and wherein at least one of the nucleic acid targets also detects at least one other genetically distinct non-target microorganism;

separately assaying the second sample portion for the presence of the target contaminant microorganism by using the multiplex PCR assay; and differentially comparing the results of the PCR assays wherein:

(a) detection of the nucleic acid targets in the multiplex PCR assay conducted on the antibody-captured first sample portion is indicative of the presence of the target contaminant microorganism in the sample, or (b) detection of none or a subset of the nucleic acid targets in the multiplex PCR assay conducted on the antibody-captured first sample portion, and the detection of the nucleic acid targets in the multiplex PCR assay conducted on the second sample portion is indicative of a composite, false positive, signal from the plurality of genetically distinct microorganisms and the absence of the target contaminant microorganism, wherein a method of confirming the presence of a particular target contaminant microorganism or of a false positive in the sample is afforded.

2. The method of claim 1, wherein the sample is contacted with a growth media to enrich the sample in the target contaminant microorganism present in the sample.

3. The method of claim 1, wherein the sample has been analyzed for the presence of the target contaminant microorganism by a 4-band multiplex PCR assay prior to contacting the first portion of the sample with the magnetic bead.

4. The method of claim 1, wherein the sample is a sample presumptively positive for the target contaminant microorganism, based on a prior test of the sample.

5. The method of claim 1, wherein assaying the antibody-captured first sample portion and separately assaying the second sample portion comprises use of a 4-band multiplex PCR assay using three PCR primer pairs complementary to three nucleic acid targets indicative of the presence of the target contaminant microorganism, and wherein one of the PCR primer pairs detects the target contaminant microorganism and the at least one other genetically distinct non-target microorganism, and wherein:
   (a) detection of the three nucleic acid targets indicative of the target contaminant microorganism in the 4-band multiplex PCR assays conducted on the antibody-captured first sample portion is indicative of the presence of the target contaminant microorganism in the sample, or
   (b) detection of the one nucleic acid target present on both the target contaminant microorganism and the at least one other genetically distinct non-target microorganism in the 4-band multiplex PCR assay conducted on the antibody-captured first sample portion, and the detection of the three nucleic acid targets indicative of the target contaminant microorganism in the 4-band multiplex PCR assay conducted on the second sample portion is indicative of a composite signal from the plurality of genetically distinct microorganisms and the absence of the target contaminant microorganism.

6. The method of claim 5, further comprising:
   providing to the 4-band multiplex PCR, an additional primer pair complementary to an additional nucleic acid target specific to the target contaminant microorganism so as to create a 5-band multiplex PCR assay;
   wherein said separately assaying the antibody-captured first sample portion for the presence of the target contaminant microorganism uses the 5-band multiplex PCR assay;
   wherein said separately assaying the second sample portion for the presence of the target contaminant microorganism uses the 5-band multiplex PCR assay; and
   differentially comparing the results of the PCR assays wherein:
   (a) detection of the four nucleic acid targets specific to the target contaminant microorganism in the 5-band multiplex PCR assay conducted on the antibody-captured first sample portion is indicative of the presence of the target contaminant microorganism in the sample, or
   (b) detection of none or a subset of the four nucleic acid targets specific to the target contaminant microorganism in the 5-band multiplex PCR assay conducted on the antibody-captured first sample portion, and the detection of all of the nucleic acid targets in the 5-band multiplex PCR assay conducted on the second sample portion is indicative of a composite signal from the plurality of genetically distinct microorganisms and the absence of the target contaminant microorganism.

7. The method of claim 1, wherein the target contaminant microorganism is selected from the group consisting of *Escherichia coli* 0157117 (*E. coli* 0157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella*, *Listeria*, *Yersinis*, *Campylobacter*, Clostridial species, *Staphylococcus* spp.; frank and opportunistic bacterial, fungal, viral, parasitic pathogens; indicator organisms including heterotrophes, generic *E. coli*, total and fecal coliforms and *enterococcus*; spoilage organisms including *Pseudomonas; Staph. aureus, Bacillus cereus, Clostridium botulinum, Clostridium perfringes, Vibrio cholerae* and *V. parahemolyticus, Yersinia enterocolitica, Yersinia pestis, Brucella, Francisella, Aeromonas, Plesiomonas, Citrobacter, Enterobacter, Klebsiella, Morganella, Proteus, Providencia, Serratia, Shigella*, and combinations thereof.

8. The method of claim 7, wherein the target contaminant microorganism is selected from the group consisting of *Escherichia coli* 0157:H7 (*E. coli* 0157:H7), enterohemorrhagic *Escherichia coli* (EHEC), enterotoxigenic *Escherichia coli* (ETEC), enteroinvasive *Escherichia coli* (EIEC), enterpathogenic *Escherichia coli* (EPEC), *Salmonella*, *Listeria*, *Yersinis*, *Campylobacter*, Clostridial species, and *Staphylococcus* spp.

9. The method of claim 8, wherein the target contaminant microorganism is *Escherichia coli* 0157:1-17 (*E. coli* 0157:H7).

* * * * *